United States Patent [19]
Yoneyoshi et al.

[11] Patent Number: 5,510,519
[45] Date of Patent: Apr. 23, 1996

[54] OPTICALLY ACTIVE SECONDARY AMINE COMPOUND, PROCESS FOR PRODUCING OPTICALLY ACTIVE SECONDARY AMINE COMPOUND AND PROCESS FOR PRODUCING OPTICALLY ACTIVE CARBOXYLIC ACID BY USING SAID COMPOUND

[75] Inventors: Yukio Yoneyoshi; Junko Kudo, both of Misawa; Toshio Nishioka, Toyonaka, all of Japan

[73] Assignee: Sumitomo Chemical Company, Limited, Osaka, Japan

[21] Appl. No.: 165,716

[22] Filed: Dec. 13, 1993

Related U.S. Application Data

[62] Division of Ser. No. 863,976, Apr. 6, 1992, Pat. No. 5,298,660.

[30] Foreign Application Priority Data

Apr. 8, 1991 [JP] Japan ................................. 3-075096
Nov. 27, 1991 [JP] Japan ................................. 3-312490

[51] Int. Cl.$^6$ .......................... C07B 57/00; C07C 209/88; C07C 209/40
[52] U.S. Cl. .................. 562/401; 564/302; 564/304; 564/355; 564/373
[58] Field of Search ............. 562/401; 564/302, 564/304, 355, 373

[56] References Cited

U.S. PATENT DOCUMENTS

| | | | |
|---|---|---|---|
| 3,739,019 | 6/1973 | Ueda et al. | 562/401 |
| 3,842,125 | 10/1974 | Horiuchi et al. | 562/401 |
| 4,259,521 | 3/1981 | Kazan et al. | 562/401 |
| 4,336,352 | 6/1982 | Naumann | 562/401 |

FOREIGN PATENT DOCUMENTS

| | | |
|---|---|---|
| 0006187 | 1/1980 | European Pat. Off. . |
| 0105696 | 4/1984 | European Pat. Off. . |
| 0423467 | 4/1991 | European Pat. Off. . |
| 49-109344 | 10/1974 | Japan . |
| 63-35540 | 2/1988 | Japan . |

OTHER PUBLICATIONS

Campbell and Harper, "The Chyrsanthemumcarboxylic acids", J. Sci Food and Agric, 3, (Apr. 3, 1942), pp. 189–192.

Hiroi et al., "Studies on Chiral Organo-Sulfur Compounds. I Asymmetric Synthesis of Sulfoxides with Optically Active-o-Aminoalkylphenol Derivatives", Chem. Pharm. Bull., vol. 31, No. 10, (1983) pp. 3471–3485.

*Primary Examiner*—Richard L. Raymond
*Assistant Examiner*—B. Bembenick
*Attorney, Agent, or Firm*—Watson Cole Stevens Davis

[57] ABSTRACT

Disclosed are optically active secondary amine compounds and salts thereof having the general formula (I):

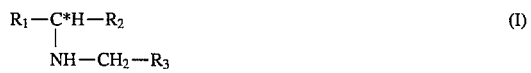

a process for the preparation of the optically active secondary amine compounds and salts thereof, and the use of such compounds. Such compounds exhibit a high resolution power and hence are useful agents for optical resolution.

12 Claims, No Drawings

OPTICALLY ACTIVE SECONDARY AMINE COMPOUND, PROCESS FOR PRODUCING OPTICALLY ACTIVE SECONDARY AMINE COMPOUND AND PROCESS FOR PRODUCING OPTICALLY ACTIVE CARBOXYLIC ACID BY USING SAID COMPOUND

This is a division of application Ser. No. 07/863,976, filed Apr. 6, 1992, (now U.S. Pat. No. 5,298,660.

The present invention relates to novel optically active secondary amine compounds and salts thereof having the general formula (I):

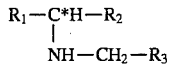
(I)

wherein $R_1$ represents a naphthyl or cyclohexyl group, or a phenyl group optionally substituted by halogen, nitro, lower alkyl or lower alkoxy, $R_2$ represents a lower alkyl group or a benzyl group optionally substituted by lower alkyl, $R_3$ represents a p-hydroxyphenyl or 2-hydroxy-3-lower alkoxyphenyl group when $R_2$ is lower alkyl, or $R_3$ represents a p-hydroxyphenyl group when $R_2$ is benzyl optionally substituted by lower alkyl, and C* represents an asymmetric carbon atom.

This invention also relates to a process for the preparation of said optically active secondary amine compounds and salts thereof, and to the use of such compounds.

It is known, for instance, from the disclosure of Japanese Patent Application Kokoku Nos. 20382-1971 and 37130-1979 and Japanese Patent Application Kokai No. 35540-1988 that a number of optically active primary amine compounds, such as α-phenyl-β-tolylethylamine, α-phenylethylamine, α-naphthylethylamine and the like, can be used as agents for the optical resolution of compounds having carboxylic acid groups.

The present inventors have synthesized various derivatives of the above-mentioned optically active amine compounds to investigate the properties of these derivatives, and have now found that a specific kind of optically active secondary amine compounds, having a hydroxybenzyl group bonded to the nitrogen atom, exhibit a resolution ability higher than that of the corresponding optically active primary amine compounds, and hence are useful agents for the optical resolution. The present invention has been accomplished on the basis of the above finding and additional extensive studies.

Thus, according to the present invention, there are provided novel optically active secondary amine compounds and salts thereof having the general formula (I):

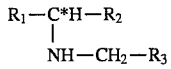
(I)

wherein $R_1$ represents a naphthyl or cyclohexyl group, or a phenyl group optionally substituted by halogen, nitro, lower alkyl or lower alkoxy, $R_2$ represents a lower alkyl group or a benzyl group optionally substituted by lower alkyl, $R_3$ represents a p-hydroxyphenyl or 2-hydroxy-3-lower alkoxyphenyl group when $R_2$ is lower alkyl, or $R_3$ represents a p-hydroxyphenyl group when $R_2$ is benzyl optionally substituted by lower alkyl, and C* represents an asymmetric carbon atom, and also provides a process for the preparation of said amine compounds, and the use of such compounds.

Now, a detailed explanation will be given for the present invention.

The optically active secondary amine compounds according to the invention are represented by the general formula (I).

Examples of the substituent represented by $R_1$ include naphthyl, cyclohexyl, phenyl, halogen-substituted phenyl such as o-, m- or p-chlorophenyl, o-, m- or p-bromophenyl or the like, nitro-substituted phenyl such as o-, m- or p-nitrophenyl or the like, lower alkyl-substituted phenyl such as o-, m- or p-tolyl, o-, m- or p-ethylphenyl, o-, m- or p-propylphenyl or the like, and lower alkoxy-substituted phenyl such as o-, m- or p-methoxyphenyl, o-, m- or p-ethoxyphenyl, o-, m- or p-propoxyphenyl or the like.

Examples of the substituents represented by $R_2$ include lower alkyl such as methyl, ethyl, propyl, butyl, pentyl or the like, benzyl, and lower alkyl-substituted benzyl such as o-, m- or p-tolylmethyl, o-, m- or p-ethylphenylmethyl, o-, m- or p-propylphenylmethyl, o-, m- or p-butylphenylmethyl, o-, m- or p-pentylphenylmethyl or the like.

Examples of the substituents represented by $R_3$ are p-hydroxyphenyl, 2-hydroxy-3-methoxyphenyl, 2-hydroxy-3-ethoxyphenyl, 2-hydroxy-3-propoxyphenyl, 2-hydroxy-3-butoxyphenyl, 2-hydroxy-3-pentoxyphenyl, etc.

As representative examples of the compounds according to the invention, there may be mentioned N-(p-hydroxybenzyl)-1-phenylethylamine, N-(p-hydroxybenzyl)- 1-(p-tolyl)ethylamine, N-(p-hydroxybenzyl)-1 -(p-isopropylphenyl)ethylamine, N-(p-hydroxybenzyl)-1 -(p-nitrophenyl)ethylamine, N-(p-hydroxybenzyl)-1 -(p-bromophenyl)ethylamine, N-(p-hydroxybenzyl)-1 -(1-naphthyl)ethylamine, N-(p-hydroxybenzyl)-1-cyclohexylethylamine, N-(p-hydroxybenzyl)-1-(p-methoxyphenyl)ethylamine, N-(2-hydroxy-3-methoxybenzyl)-1-phenylethylamine, N-(2-hydroxy-3-methoxybenzyl)-1 -(p-tolyl)ethylamine, N-(2-hydroxy-3-methoxybenzyl)-1 -(p-isopropylphenyl)ethylamine, N-(2-hydroxy-3-methoxybenzyl)-1 -(p-nitrophenyl)ethylamine, N-(2-hydroxy- 3-methoxybenzyl)-1-(p-bromophenyl)ethylamine, N-(2-hydroxy-3-methoxybenzyl)-1-(1-naphthyl)ethylamine, N-(2-hydroxy-3-methoxybenzyl)-1-cyclohexylethylamine, N-(2-hydroxy-3-methoxybenzyl)-1-(p-methoxyphenyl)ethylamine, N-(p-hydroxybenzyl)-α-phenyl-β-p-tolylethylamine and the like.

The optically active secondary amine compounds (I) may be prepared by a process, wherein an optically active amine of the general formula (II):

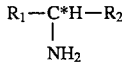
(II)

wherein $R_1$, $R_2$ and C* have the meanings stated above, is reacted with a hydroxybenzaldehyde of the general formula (III):

(III)

wherein $R_3$ has the meaning stated above, to produce an imine compound of the general formula (IV):

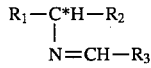
(IV)

wherein $R_1$, $R_2$, $R_3$ and C* have the meanings stated above, and said imine compound is then subjected to a reduction process.

Examples of salts of the optically active compounds (I) includes salts of the amine compounds with inorganic acids such as hydrochloric acid, sulfuric acid, nitric acid and the like.

In carrying out the reactions of the optically active compounds (II) with the hydroxybenzaldehydes (III) to form the imine compounds (IV), it is possible to use, as the optically active amine (II), 1-phenylethylamine, 1-(1-naphthyl)ethylamine, 1-cyclohexylethylamine, 1-(p-tolyl)ethylamine, 1-(p-isopropylphenyl)ethylamine, 1-(p-nitrophenyl)ethylamine, 1-(p-bromophenyl)ethylamine, α-ethylbenzylamine, α-isopropylbenzylamine, 1-(β-naphthyl)ethylamine, α-phenyl-β-p-tolylethylamine, etc. They are known compounds and will be easily available. Examples of the hydroxybenzaldehydes (III) include p-hydroxybenzaldehyde, 2-hydroxy-3-methoxybenzaldehyde and the like.

Usually, the reaction is carried out in an organic solvent. Examples of such solvents include aromatic hydrocarbons such as benzene, toluene, xylene, etc., halogenated hydrocarbons such as carbon tetrachloride, chloroform, etc., alcohols such as methanol, ethanol, isopropanol and the like, and ethers such as diethyl ether, tetrahydrofuran, etc. These solvents may be used alone or in the form of a mixture thereof.

The reaction temperature is generally within 0° to 200° C., preferably 0' to 150° C. Usually, the object of the reaction will be satisfactorily accomplished if the reaction time is within 0.5 to 30 hours, preferably 0.5 to 10 hours.

The imine compounds (IV) thus obtained may be isolated, or may be used in the next reaction step without being separated therefrom.

In the next step, the imine compounds (IV) are reduced so as to produce the optically active amine compounds (I). This reduction may generally be carried out by using a reducing agent such as metal hydrides, or by catalytic hydrogenation.

In the case of a process using a reducing agent, it is possible to employ metal hydrides such as lithium aluminum hydride, sodium borohydride and boranes, for instance, diborane, borane-THF, borane-sulfide complexes, borane-amine complexes and the like.

When lithium aluminum hydride or sodium borohydride is used as the reducing agent, the amount thereof used may generally be within 0.25 to 5 moles, preferably 0.25 to 2 moles per i mole of the imine compounds.

In the case of boranes, they may usually be used within a range of 0.3 to 5 moles, preferably 0.3 to 3 moles expressed as boron per 1 mole of the imine compounds.

The reduction is generally carried out in a solvent. The solvents should be preferably those inert to the reduction, and include, for example, ethers such as diethyl ether, diglyme, triglyme, tetrahydrofuran, dioxane, etc., aromatic hydrocarbons such as benzene, toluene, xylene, etc., and halogenated hydrocarbons such as methylene chloride, 1,2-dichloroethane, chloroform, etc. These solvents may be used alone or in the form of a mixture thereof.

When effecting the reduction by using sodium borohydride as the reducing agent, it is possible to use not only the above-mentioned solvents but also lower alcohols. There is no specific limitation in the amount of the solvents used.

The reaction temperature is generally within a range of −50° to +100° C., preferably −20° to +100° C. The reaction time is not particularly limited.

After the completion of the reaction, the reaction mixture is decomposed with water, acetic acid or an inorganic acid. Then the reaction mixture is alkalized, and organic layer is separated under neutral or weakly alkaline conditions, which is thereafter concentrated to obtain the optically active amine compounds (I). If necessary, it is possible to effect a purification operation, including, for instance, a recrystallization, a column chromatography using silica gel and the like.

In the case of the catalytic hydrogenation, use may be made of a reduction catalyst, including, for example, Raney nickel, palladium-carbon, platinum dioxide, platinum black and the like. These catalysts may be used generally within a range of 0.1 to 100% by weight, preferably from 0.5 to 50% by weight on the basis of the weight of the imine compounds (IV).

Though the solvent to be used is not particularly restricted. As long as it does not paison the catalyst, usually alcohols such as methanol, ethanol, etc., ethers such as diethyl ether, tetrahydrofuran, dioxane and the like, acetate esters such as ethyl acetate, isoamyl acetate, butyl acetate, etc., aromatic hydrocarbons such as benzene, toluene, xylene and the like, acetic acid, N-methylpyrrolidone, water, etc. These solvents may be used alone or as a mixture thereof. There is no specific limitation in the amount of the solvents used.

The reaction temperature is generally within a range of −30° to +150° C., preferably −10° to +100° C. The reaction pressure is usually within a range 0 to 100 kg/cm$^2$ preferably between 0 to 50 kg/cm$^2$. The reaction time is not particularly limited.

After the reduction is carried out in this way, the catalyst is removed by filtration, the optically active ámine compounds (I) is obtained by evaporation of the filtrate. If necessary, it is effect a purification, including, for example, a recrystallization and a column chromatography using silica gel or the like.

The compounds (I) according to the invention are useful as agents for the optical resolution. For instance, if any one of the compounds according to the invention is reacted with (±)-chrysanthemic acid, and if the resulting salt is subjected to an optical resolution, then (+)-chrysanthemic acid will be obtained.

Furthermore, if a compound according to the invention is reacted with a (±)-α-substituted phenylacetic acid, for instance, (±)-ibuprofen, (±)-naproxen, (±)-flurbiproten, (±)-ketoprofen, (±)-2-(4-chlorophenyl)isovaleric acid or the like, (±)-cis-permethric acid, (±)-trans-permethric acid, or an α-hydroxy-acid such as (±)-2-hydroxy-4-phenylbutanoic acid, (±)-mandelic acid or the like, and if the resulting amine salt is thereafter subjected to an optical resolution, then the corresponding optically active (+)-α-transpermethric acid or (−)-α-hydroxy-acid will be obtained.

As examples of the compounds according to the invention, which are very desirable as agents for the optical resolution of (±)-chrysanthemic acid, (±)-permethric acid and (±)-2-(4-chlorophenyl)isovaleric acid, there may be mentioned (R)-N-(p-hydroxybenzyl)-1-phenylethylamine, (R)-N-(p-hydroxybenzyl)-1-naphthylethylamine, (S)-N-(p-hydroxybenzyl)-1-cyclohexylethylamine, (R)-N-(p-hydroxybenzyl)-1-(p-tolyl)ethylamine, (R)-N-(p-hydroxybenzyl)-1-(p-nitrophenyl)ethylamine, (R)-N-(p-hydroxybenzyl)-1-(p-bromophenyl)ethylamine, (R)-N-(2-hydroxy-3-methoxybenzyl)-1-phenylethylamine, (R)-N-(2-hydroxy-3-methoxybenzyl)-1-(p-tolyl)ethylamine, (R)-N-(2-hydroxy-3-methoxybenzyl)-1-(p-nitrophenyl)ethylamine, (R)-(+)-N-p-hydroxybenzyl-α-phenyl-α -p-tolylethylamine and the like. When the optical resolution of (±)-ketoprofen or (±)-mandelic acid is carried out, it is advantageous to use, as agents for the optical resolution, the compounds according to the invention, with the proviso that the compounds used for this purpose should have a steric configuration opposite to that of the compounds listed in the above.

As (±)-chrysanthemic acid, use may be made of (±)-trans-chrysanthemic acid or (±)-cis/trans-mixed-chrysanthemic acid generally within a range of a cis/trans ratio of 0/100 to 50/50, preferably 0/100 to 40/60.

An optical resolution of (±)-chrysanthemic acid, (±)-cis-permethric acid, (±)-trans-permethric acid, (±)-α-hydroxy-acid, (±)-α-substituted phenylacetic acid as the like is generally carried out in a solvent. Examples of solvents used are aromatic hydrocarbons such as benzene, toluene, xylene and the like, aliphatic hydrocarbons such as hexane, heptane, etc., alcohols such as methanol, ethanol, etc., ketones such as acetone, methyl isobutyl ketone and the like, ethers such as tetrahydrofuran, dioxane, etc., and a mixture of these solvents as well as a mixture of the solvents with water.

In carrying out an optical resolution, use is made of the optically active amine compounds as the agents for optical resolution within a range of 0.2 to 1.2 moles, preferably 0.3 to 1.1 moles per 1 mole of (±)-chrysanthemic acid, (±)-cis-permethric acid, (±)-trans-permethric acid, (±)-α-hydroxy-acids or (±)-α-substituted phenylacetic acids.

In the case of the optical resolution of (±)-chrysanthemic acid, (±)-cis-permethric acid, (±)-trans-permethric acid and (±)-2-(4-chlorophenyl)isovaleric acid, it is possible to carry out a process, wherein such a substance is dissolved, together with (R)-isomers of the optically active amine compounds (I), in any of the above-mentioned solvents, and then kept standing or stirred. The temperature is generally within a range of −20° to +150° C., preferably −10° to +100° C., with the proviso that when $R_1$=cyclohexyl, then use is made of (S)-isomers of the amine compounds (I). In the case of the optical resolution of (±)-ketoprofen or (±)-mandelic acid, use is usually made of (S)-isomers of the amine compounds (I), except that, when $R_1$=cyclohexyl, then use is made of (R)-isomers of the amine compounds (I).

After that, the crystalline materials thus produced are separated by filtration, and decomposed with an acid such as hydrochloric acid, sulfuric acid or the like. Thereafter, an extraction operation is carried out with organic solvents to give (+)-transchrysanthemic acid, (+)-cis-permethric acid, (+)-transpermethric acid, (−)-mandelic acid, (+)-α-substituted phenylacetic acid or the like. On the other hand, the aqueous layer is alkalized and subjected to an extraction operation, whereby the (R)- or (S)-isomers of the optically active amine compounds may be easily recovered for the reuse thereof.

Alternatively, if the salts thus formed are decomposed with a base such as sodium hydroxide or the like, and if the resultant products are then extracted with organic solvents under alkaline conditions, then the optically active amine compounds may be recovered. On the other hand, the aqueous layer is acidified, and then subjected to an extraction operation to give (+)-trans-chrysanthemic acid, (+)-cis-permethric acid, (+)-trans-permethric acid, (−)-α-hydroxy-acid, (+)-α-substituted phenylacetic acid or the like.

The optically active amine compounds of the general formula (I) according to the invention have good properties as agents for the optical resolution, and are very desirable for the use thereof in industrial fields. Furthermore, the optically active amine compounds mentioned above can advantageously be prepared according to the invention even on an industrial acale.

Next, the invention will be illustrated in more detail by the Examples. However, it should be noted that the invention is not limited only to the Examples.

EXAMPLES 1

9.96 g (0.082 mole) of (R)-(+)-1-phenylethylamine and 10.54 g (0.086 mole) of p-hydroxybenzaldehyde were dissolved in 140 ml of ethyl alcohol, and the resulting solution was stirred under reflux for 2 hours. The reaction mixture was cooled to room temperature, and the crystalline material thus formed was separated by filtration to give 13.0 g of (−)-N-(p-hydroxybenzylidene)- 1-phenylethylamine. Yield: 70.4%. m.p. 176°–178° C.; $[\alpha]_D^{22}$ −120.7° (C 1.0, MeOH) NMR-spectral data (δ ppm, DMSO-$d_6$) 1.50 (d) 3H; 4.50 (q) 1H; 6.7–7.8 (m) 9H; 7–7.8 (broad) 1H; 8.34 (s) 1H

EXAMPLE 2

15 g (0.111 mole) of (R)-(+)-(p-tolyl)ethylamine and 14.23 g (0.117 mole) of p-hydroxybenzaldehyde were dissolved in 200 ml of ethyl alcohol, and the resultant solution was stirred at room temperature for 2 hours and then stirred under reflux for 2 hours. The reaction mixture was concentrated under reduced pressure to give 27.2 g of a crude crystalline product comprising (R)-(−)-N-(p-hydroxybenzylidene)-1-(p-tolyl)ethylamine. The crude product was recrystallized from ethyl alcohol to obtain 20.6 g of the aimed product. Yield: 77.7%. m.p. 168°–170° C.; $[\alpha]_D^{24}$ −118.0° (C 1.0, MeOH) NMR-spectral data (δ ppm, DMSO-$d_6$) 1.48 (d) 3H; 2.29 (s) 3H; 4.94 (q) 1H; 6.7–7.8 (m) 9H; 8.28 (s) 1H EXAMPLE 3

The procedures shown in Example 2 were repeated, except that 5.34 g of (R)-(+)-(p-nitrophenyl)ethylamine were used instead of 15 g of (R)-(+)-1 -(p-tolyl)ethylamine, and that 5.13 g of 2-hydroxy-3-methoxybenzaldehyde were used instead of 14.23 g of p-hydroxybenzaldehyde.

9.14 g of (R)-(−)-N-(2-hydroxy-3-methoxybenzylidene)-1 -(p-nitrophenyl)ethylamine were obtained. Yield: 94.7%. m.p. 88°–90° C.; $[\alpha]_D^{25}$ −223.0° (C 1.0, $CHCl_3$) NMR-spectral data (δ ppm, $CDCl_3$) 1.66 (d) 3H; 3.94 (s) 3H; 4.67 (m) 1H; 6.8–7.05 (m) 3H; 7.4–8.35 (m) 4H; 8.49 (s) 1H; 13.6 (s) 1H

EXAMPLE 4

4.44 g (0.0222 mole) of (R)-(+)-1-(p-bromophenyl)ethylamine and 2.85 g (0.0233 mole) of p-hydroxybenzaldehyde were dissolved in 30 ml of ethyl alcohol, and the solution thus formed was stirred under reflux for 3 hours. After the completion of the reaction, the reaction mixture was concentrated under reduced pressure, and refined by a column chromatography using 30 g of silica gel to give 6.75 g of (−)-N-(p-hydroxybenzylidene)- 1-(p-bromophenyl)ethylamine. Yield: 97.9%. m.p. 156°–161° C.; $[\alpha]_D^{25}$ −87.6° (C 0.7, $CHCl_3$) NMR-spectral data (δ ppm, DMSO-$d_6$) 1.48 (d) 3H; 4.34 (q) 1H; 6.75–7.9 (m) 9H;

EXAMPLE 5

The procedures shown in Example 4 were repeated, except that 5.32 g of (R)-(+)-(p-nitrophenyl)ethylamine were used instead of 4.44 g of (R)-(+)-1 -(p-bromophenyl)ethylamine, and that the amount of p-hydroxybenzaldehyde used was 4.10 g.

8.62 g of (−)-N-(p-hydroxybenzylidene)-1 -(p-nitrophenyl)ethylamine were obtained. Yield: 99.7%. m.p. 118°–119.5° C.; $[\alpha]_D^{25}$ −105.3° (C 1.0, $CHCl_3$) NMR-spectral data (δ ppm, $CDCl_3$) 1.65 (d) 3H; 4.63 (q) 1H; 6.55–7.0 (m) 4H; 7.4–8.3 (m) 9H; 8.31 (s) 1H

EXAMPLE 6

The procedures shown in Example 4 were repeated, except that 7.63 g of (S)-(+)-1-cyclohexylethylamine were used instead of 4.44 g of (R)-(+)-1-(p-bromophenyl)ethylamine, and that the amount of p-hydroxybenzaldehyde used was 7.69 g.

15.98 g of (+)-N-(p-hydroxybenzylidene)-1-cyclohexylethylamine were obtained. Yield: 94.8%. m.p. 130.5°–132° C.; $[\alpha]_D^{25}$+122.7° (C 1.0, CHCl$_3$) NMR-spectral data ($\delta$ ppm, CDCl$_3$) 0.5–2.05 (broad) 11H; 1.29 (d) 3H; 3.03 (q) 1H; 6.4–7.7 (m) 4H; 8.07 (s) 1H; 9.17 (s) 1H

EXAMPLE 7

The procedures shown in Example 4 were repeated, except that 9.27 g of (S)-(+)-1-cyclohexylethylamine were used instead of 4.44 g of (R)-(+)-1 -(p-bromophenyl)ethylamine, and that 11.64 g of 2-hydroxy-3-methoxybenzaldehyde were used instead of 4.44 g of p-hydroxybenzaldehyde.

18.59 g of (+)-N-(2-hydroxy-3-methoxybenzylidene)-1-cyclohexylethylamine were obtained. Yield: 97.6%. $[\alpha]_D^{26}$+132.2° (C 1.0, CHCl$_3$) NMR-spectral data ($\delta$ ppm, CDCl$_3$) 0.5–2.0 (broad) 11H; 1.28 (d) 3H; 3.15 (m) 1H; 3.90 (s) 1H; 6.84 (m) 3H; 8.65 (s) 1H; 14.0–14.8 (broad) 1H

EXAMPLE 8

The procedures shown in Example 4 were repeated, except that 13.67 g of (R)-(+)-1-(1-naphthyl)ethylamine were used instead of 4.44 g of (R)-(+)-1 -(p-bromophenyl)ethylamine, and that 12.75 g of 2-hydroxy-3-methoxybenzaldehyde were used instead of 4.44 g of p-hydroxybenzaldehyde.

23.42 g of (–)-N-(2-hydroxy-3-methoxybenzylidene)-1-(1-naphthyl)ethylamine were obtained. Yield: 96.1%. $[\alpha]_D^{23}$–327.9° (C 1.0, CHCl$_3$) NMR-spectral data ($\delta$ ppm, CDCl$_3$) 1.76 (d) 3H; 3.87 (s) 3H, 5.36 (q) 1H; 6.6–7.0 (m) 3H; 7.2–8.2 (m) 7H; 8.35 (s) 1H; 13.5–14.5 (broad) 1H

EXAMPLE 9

The procedures shown in Example 4 were repeated, except that 6.76 g of (R)-(+)-1-(1-tolyl)ethylamine were used instead of 4.44 g of (R)-(+)-1 -(p-bromophenyl)ethylamine, and that 7.99 g of 2-hydroxy-3-methoxybenzaldehyde were used instead of 4.44 g of p-hydroxybenzaldehyde.

12.77 g of (–)-N-(2-hydroxy-3-methoxybenzylidene)-1-(p-tolyl)ethylamine were obtained. Yield: 94.8%. $[\alpha]_D^{27}$–211.7° (C 1.0, CHCl$_3$) NMR-spectral data ($\delta$ ppm, CDCl$_3$) 1.61 (d) 3H; 2.33 (s) 3H, 3.90 (s) 3H; 4.53 (q) 1H; 6.7–7.0 (m) 3H; 7.0–7.4 (m) 4H; 8.36 (s) 1H; 13.4–14.6 (broad) 1H

EXAMPLE 10

The procedures shown in Example 4 were repeated, except that 7.27 g of (R)-(+)-1-phenylethylamine were used instead of 4.44 g of (R)-(+)-1 -(p-bromophenyl)ethylamine, and that 9.58 g of 2-hydroxy-3-methoxybenzaldehyde were used instead of 4.44 g of p-hydroxybenzaldehyde.

14.58 g of (–)-N-(2-hydroxy-3-methoxybenzylidene)-1-phenylethylamine were obtained. Yield: 95.2%. $[\alpha]_D^{27}$–215.8° (C 1.0, CHCl$_3$) NMR-spectral data ($\delta$ ppm, CDCl$_3$) 1.41 (d) 3H; 3.5–4.05 (m) 3H; 3.90 (s) 3H; 5.5–6.5 (broad) 2H; 6.34–6.9 (m) 3H; 7.32 (s) 5H

EXAMPLE 11

21.13 g (0.1 mole) of (S)-(+)-α-phenyl-β -p-tolylethylamine (optical purity: 98.2%) and 12.82 g (0.105 mole) of p-hydroxybenzaldehyde were dissolved in 100 ml of toluene, and the solution thus formed was stirred under reflux for 2 hours, while the water formed during the reaction was azeotropically distilled off. Then the reaction mixture was cooled to room temperature, and the crystalline material thus formed was separated by filtration and recrystallized from ethyl acetate to give 17.09 g of an imine compound as colorless crystals. Yield: 54.2%. m.p. 202°–204° C.; $[\alpha]_D^{25}$–129.4° (C 1.0, EtOH) NMR-spectral data ($\delta$ ppm, DMSO-d$_6$) 2.25 (s) 3H; 3.10 (d) 2H; 4.50 (t) 1H; 6.7–7.7 (m) 9H; 7.0 (s) 4H; 8.0 (s) 1H; 8.7–10.5 (broad) 1H

EXAMPLE 12

15.0 g (0.124 mole) of (R)-(+)-1-phenylethylamine and 19.8 g (0.13 mole) of 2-hydroxy-3-methoxybenzaldehyde were dissolved in 300 ml of ethyl alcohol, and the resultant solution was stirred at room temperature for 3 hours, and then stirred under reflux for 2 hours. After that, 2.35 g (0.062 mole) of sodium borohydride were added at room temperature to the reaction mixture, which was then stirred at a temperature of from 30° to 35° C. for 1 hour, and thereafter stirred at a temperature of from 55° to 60° C. for 1.5 hours. After the completion of the reaction, 50 ml of a 10% hydrochloric acid were added at room temperature.

The reaction mixture was then concentrated under reduced pressure, and the resulting residue was dissolved in 150 ml of water. The aqueous solution thus formed was washed with 150 ml of toluene, and the aqueous layer was neutralized or weakly alkalized with a 23% aqueous odium hydroxide solution. The toluene layer was washed with water, and concentrated under reduced pressure to give 31.41 g of (R)-(+)-N-(2-hydroxy-3-methoxybenzyl)- 1-phenylethylamine as oily substance. Yield: 98.6%. $[\alpha]_D^{20}$+29.6° (C 1.0, CHCl$_3$) NMR-spectral data ($\delta$ ppm, CDCl$_3$) 1.42 (d) 3H; 3.5–4.05 (m) 3H; 3.89 (s) 3H; 5.5–6.5 (broad) 2H; 6.35–6.9 (m) 3H; 7.32 (s) 5H

EXAMPLE 13

The procedures of Example 12 were repeated, except that 13.67 g of (R)-(+)-1-(1-naphthyl)ethylamine were used instead of 15.0 g of (R)-(+)-1-phenylethylamine, and that 12.75 g of 2-hydroxy-3-methoxybenzaldehyde were employed instead of 19.8 g of 2-hydroxy- 3-methoxybenzaldehyde.

(R)-(–)-N-(2-hydroxy-3-methoxybenzyl)-1 -(1-naphthyl)ethylamine was obtained in an amount of 23.67 g. Yield: 96.5%. $[\alpha]_D^{25}$–42.5° (C 1.0, CHCl$_3$) NMR-spectral data ($\delta$ ppm, CDCl$_3$) 1.56 (d) 3H; 3.87 (s) 3H; 4.70 (q) 1H; 5.68–7.0 (broad) 2H; 6.3–6.9 (m) 3H; 7.1–8.2 (m) 7H

EXAMPLE 14

8.5 g (0.0283 mole) of (R)-(–)-N-(2-hydroxy-3 -methoxybenzylidene)-1-(p-nitrophenyl)ethylamine were dissolved in 150 ml of ethyl alcohol. Then, 0.54 g (0.0143 mole) of sodium borohydride was added at room temperature to the reaction mixture, which was thereafter stirred at a temperature of from 30° to 35° C. for 2 hours, and then stirred at a temperature of from 55° to 60° C. for 2 hours. After the completion of the reaction, the reaction mixture was admixed with 30 ml of a 10% hydrochloric acid, and then concentrated under reduced pressure. The resulting residue was dissolved in 150 ml of water, washed with 100 ml of toluene, and separated into individual layers. The aqueous layer was neutralized or weakly alkalized with a 20% aqueous sodium hydroxide solution, and extracted twice with 100 ml of toluene. The toluene layer was washed with water, and concentrated under reduced pressure to give 7.75 g of (R)-(+)-N-(2-hydroxy-3-methoxybenzyl)-1-(p-nitrophenyl)ethylamine as crystalline substance. Yield: 90.6%. m.p. 112.5°–113.56° C.; $[\alpha]_D^{24}$+64.0° (C 1.0, CHCl$_3$) NMR-spectral data (δ ppm, CDCl$_3$) 1.46 (d) 3H; 3.5–4.2 (m) 3H; 3.9 (s) 3H; 5.0–6.4 (broad) 1H; 6.4–6.9 (m) 3H 7.35–8.4 (m) 4H (s)

EXAMPLE 15

The procedures shown in Example 14 were repeated, except that 18.0 g of (S)-(+)-N-(2-hydroxy-3-methoxybenzylidene)-1-cyclohexylethylamine were used instead of 8.5 g of (R)-(–)-N-(2-hydroxy-3-methoxybenzylidene)- 1-(p-nitrophenyl)ethylamine.

16.12 g of (S)-(+)-N-(2-hydroxy-3-methoxybenzyl)-1-cyclohexylethylamine were obtained as crystalline substance. Yield: 88.0%. m.p. 65°–66° C.; $[\alpha]_D^{23}$+3.8° (C 1.0, CHCl$_3$) NMR-spectral data (δ ppm, CDCl$_3$) 0.7–2.1 (broad) 11H; 1.12 (d) 3H; 2.64 (q) 1H; 3.89 (s) 3H; 3.9–4.1 (m) 2H; 5.9–6.6 (broad) 2H; 5.5–7.0 (m) 3H

EXAMPLE 16

The procedures shown in Example 14 were repeated, except that 24.0 g of (R)-(–)-N-(2-hydroxy-3-methoxybenzylidene)-1-(1-naphthyl)ethylamine were used instead of 8.5 g of (R)-(–)-N-(2-hydroxy-3-methoxybenzylidene)-1-(p-nitrophenyl)ethylamine.

23.69 g of (R)-(–)-N-(2-hydroxy-3-methoxybenzyl)-1-(1-naphthyl)ethylamine were obtained. Yield: 98.0%. $[\alpha]_D^{25}$–42.5° (C 1.0, CHCl$_3$) NMR-spectral data (δ ppm, CDCl$_3$) 1.56 (d) 3H; 3.87 (s) 5H; 4.70 (q) 1H; 5.4–7.3 (broad) 2H; 6.3–6.9 (m) 3H; 7.1–8.2 (m) 7H

EXAMPLE 17

11.26 g (0.05 mole) of (R)-(–)-N-(p-hydroxybenzylidene)- 1-phenylethylamine were dissolved in 150 ml of ethyl alcohol. The resulting solution was admixed with 0.95 g (0.025 mole) of sodium borohydride at room temperature, stirred at a temperature of from 30° to 35° C. for 2 hours, and then stirred at a temperature of from to 60° C. for 2 hours. After the completion of the reaction, 28 ml of a 10% hydrochloric acid were added at room temperature to the reaction mixture, which was then concentrated under reduced pressure. The residue thus obtained was admixed with 50 ml of water, and thereafter neutralized or weakly alkalized with a 20% aqueous sodium hydroxide solution. Then an extraction operation was carried out twice with 100 ml of chloroform, and the chloroform layer was washed with water, dried over sodium sulfate, and concentrated under reduced pressure to give 11.34 g of crude (R)-(+)-N-(p-hydroxybenzyl)-1-phenylethylamine. The crude product was refined by a column chromatography employing silica gel, so that 10.64 g of a refined product were obtained as viscous oil. Yield: 93.6%. $[\alpha]_D^{21}$+44.2° (C 1.0, CHCl$_3$) NMR-spectral data (δ ppm, CDCl$_3$) 1.39 (d) 3H; 3.54 (s) 2H; 3.83 (q) 1H; 5.09 (s) 2H; 6.5–7.25 (m) 4H; 7.32 (s) 5H

EXAMPLE 18

The procedures shown in Example 14 were repeated, except that 12.52 g of (R)-(–)-N-(2-hydroxy-3-methoxybenzylidene)-1-(p-tolyl)ethylamine were used instead of 8.5 g of (R)-(–)-N-(2-hydroxy-3-methoxybenzylidene)- 1-(p-nitrophenyl)ethylamine.

(R)-(+)-N-(2-hydroxy-3-methoxybenzyl)-1-(p-tolyl)ethylamine was obtained as crude crystalline product. Yield: 96.9%. The crude product was recrystallized from isopropanol to give 8.53 g of a refined product. Yield after recrystallization: 69.7%. m.p. 87°–88.5° C.; $[\alpha]_D^{25}$+42.3° (C 1.0, CHCl$_3$) NMR-spectral data (δ ppm, CDCl$_3$) 1.43 (d) 3H; 2.34 (s) 3H; 3.5–4.1 (m) 3H; 3.87 (s) 3H; 5.9–7.3 (broad) 2H; 6.35–6.85 (m) 3H; 7.15 (s) 4H

EXAMPLE 19

19.0 g (0.0794 mole) of (R)-(–)-N-(p-hydroxybenzylidene)- 1-(p-tolyl)ethylamine were dissolved in 200 ml of ethyl alcohol. The resulting solution was admixed with 1.50 g (0.04 mole) of sodium borohydride at room temperature, stirred at a temperature of from 25° to 30° C. for 1 hours, and then stirred at a temperature of from 55° to 60° C. for 1 hours. After the completion of the reaction, 47 ml of a 10% hydrochloric acid were added at room temperature to the reaction mixture, which was then concentrated under reduced pressure. The residue thus obtained was admixed with 100 ml of water, and thereafter neutralized or weakly alkalized with a 20% aqueous sodium hydroxide solution. Then an extraction operation was carried out three times with 100 ml of chloroform, and the chloroform layer was washed with water, dried over sodium sulfate, and concentrated under reduced pressure to give 18.99 g of (R)-(+)-N-(p-hydroxybenzyl)- 1-(p-tolyl)ethylamine. Yield: 99.1%. m.p. 114.5°–116° C.; $[\alpha]_D^{24}$+47.5° (C 1.0, CHCl$_3$) NMR-spectral data (δ ppm, CDCl$_3$) 1.27 (d) 3H; 2.32 (s) 3H; 3.42 (s) 2H; 3.69 (q) 1H; 6.3–7.4 (broad) 2H; 6.5–7.5 (m) 8H

EXAMPLE 20

6.26 g (0.0206 mole) of (R)-(–)-N-(p-hydroxybenzylidene)-1-(p-bromophenyl)ethylamine were dissolved in 50 ml of ethyl alcohol. The resulting solution was admixed with 0.39 g (0.0103 mole) of sodium borohydride at room temperature, stirred at a temperature of from 25° to 30° C. for 2 hours, and then stirred at a temperature of from 55° to 60° C. for 2 hours. After the completion of the reaction, 15 ml of a 10% hydrochloric acid were added at room temperature to the reaction mixture, which was then concentrated under reduced pressure. The residue thus obtained was neutralized or weakly alkalized with a 2% aqueous sodium hydroxide solution. Then an extraction operation was carried out three times with 50 ml of chloroform, and the chloroform layer was washed with water, dried over sodium sulfate, and concentrated under reduced pressure to give 6.14 g of a crude crystalline product, which was then recrystallized from toluene, so that 4.67 g of (R)-(+)-N-(p-hydroxybenzyl)- 1-(p-bromophenyl)ethylamine were obtained. Yield: 74.0%. m.p. 110°–112° C.; $[\alpha]_D^{24}$+52.2° (C 1.0, CHCl$_3$) NMR-spectral data (δ ppm, DMSO-d$_6$) 1.25 (d) 3H; 2.0–2.9 (broad) 1H; 3.40 (s) 2H; 3.69 (q) 1H; 6.5–7.7 (m) 3H; 8.7–9.6 (broad) 1H

EXAMPLE 21

17.13 g (0.10 mole) of (R)-(+)-naphthylethylamine and 12.82 g (0.105 mole) of p-hydroxybenzaldehyde were dissolved in 300 ml of ethyl alcohol, and the resultant solution was stirred under reflux for 2 hours. 1.89 g (0.05 mole) of sodium borohydride were added at room temperature to the reaction mixture, which was then stirred at room temperature for 1.5 hours, and thereafter stirred under reflux for 1 hour. After the completion of the reaction, the reaction mixture was concentrated under reduced pressure. The residue thus obtained was admixed with 100 ml of water, and extracted twice with 100 ml of ethyl acetate. The ethyl acetate layer was concentrated under reduced pressure to give 28.964 g of a crude crystalline product, which were then admixed with a 36% hydrochloric acid in methanol so as to form a hydrochloride salt of the product. The solution was concentrated under reduced pressure, and the residue thus formed was admixed with 50 ml of toluene to crystallized out the hydrochloride salt, which was then separated off by filtration, and washed twice with 50 ml of toluene to obtain 30.42 g of the crystalline product. This product was admixed with 100 ml of water, neutralized or weakly alkalized with a 20% aqueous sodium hydroxide solution, and extracted three times with 200 ml of ethyl acetate. The organic layer was washed with water, dried and concentrated under reduced pressure to give 26.99 g of (R)-(−)-N-(p-hydroxybenzyl)- 1-(1-naphthyl)ethylamine as crystals. Yield: 97.3%.

m.p. 131.5°–133° C.; $[\alpha]_D^{25}$ −3.4° (C 1.0, CHCl$_3$)

EXAMPLE 22

4.50 g (0.02 mole) of the (R)-(−)-N-(p-hydroxybenzylidene)- 1-phenylethylamine, which had been obtained in Example 1, were dissolved in 200 ml of tetrahydrofuran, and admixed with 36.4 ml (0.04 mole) of a 1.1M solution of a borane-THF complex in tetrahydrofuran. The reaction mixture was stirred at room temperature for 8 hours, and thereafter stirred at 50° C. for 2 hours.

The reaction mixture was cooled with ice, and admixed with a 10% hydrochloric acid to decompose the reaction product. Then the reaction mixture was concentrated under reduced pressure, and the resultant residue was neutralized with a 20% aqueous sodium hydroxide solution, and extracted with chloroform. The organic layer was concentrated under reduced pressure, and refined by a silica gel column chromatography to give 4.38 g of (R)-(+)-N-(p-hydroxybenzyl)-1-phenylethylamine Yield: 96.4%. $[\alpha]_D^{25}$+44.1° (C 1.0, CHCl$_3$)

EXAMPLE 23

5.63 g (0.025 mole) of (R)-(−)-N-(p-hydroxybenzylidene)- 1-phenylethylamine were dissolved in 50 ml of methanol. To this solution was added 5% by weight of a 5% Pd/C per the weight of the imine compound in an autoclave, and a catalytic hydrogenation reaction was effected under a hydrogen pressure of 20 kg/cm$^2$ at a temperature of from 25° to 30° C. for 12 hours. After the completion of the reaction, the catalyst was separated off by filtration, and the reaction mixture was concentrated under reduced pressure to obtain 5.58 g of a crude amine product, which were then refined by a silica gel column chromatography, so that 5.38 g of (R)-(+)-N-(p-hydroxybenzyl)-1-phenylethylamine were obtained. Yield: 94.7%. $[\alpha]_D^{25}$+44.2° (C 1.0, CHCl$_3$)

EXAMPLE 24

21.13 g (0.1 mole) of (R)-(−)-α-phenyl-β -p-tolylethylamine (optical purity: 100%) and 12.82 g (0.105 mole) of p-hydroxybenzaldehyde were dissolved in 750 ml of ethyl alcohol. The reaction solution thus obtained was stirred at room temperature for 3 hours, and then stirred under reflux for 1 hour. Thereafter, the reaction solution was admixed at room temperature with 1.89 g (0.05 mole) of sodium borohydride, stirred for 3 hours, and then stirred under reflux for 1 hour. The reaction mixture was admixed with 75 ml of a 10% hydrochloric acid, and then concentrated under reduced pressure to give a crude (R)-(+)-N-p-hydroxybenzyl-α -phenyl-β-p-tolylethylamine.HCl salt, which was thereafter neutralized with an aqueous sodium hydroxide solution. The resultant solution was concentrated under reduced pressure to obtain the crystals, which were then recrystallized from ethyl alcohol, so that 20.47 g of (R)-(+)-N-p-hydroxybenzyl-α-phenyl-β-p-tolylethylamine were obtained as colorless crystals. Yield: 64.5%. m.p. 129.5°–130° C.; $[\alpha]_D^{25}$+21.2° (C 1.0, CHCl$_3$) NMR-spectral data (δ ppm, CDCl$_3$) 2.29 (s) 3H; 2.94 (d) 2H; 3.49 (d) 2H; 3.89 (t) 1H; 3.37 (s) 2H; 6.35–6.90 (m) 4H; 6.99 (s) 4H; 7.30 (s) 5H

EXAMPLE 25

3.15 g (0.01 mole) of the imine compound, which had been obtained in Example 11, were dissolved in 100 ml of tetrahydrofuran, and admixed at room temperature with 20 ml (0.02 mole) of a 1.0M solution of a borane-THF complex in tetrahydrofuran. The reaction mixture was stirred at room temperature for 10 hours, and then stirred at 50° C. for 2 hours. Then the reaction mixture was cooled with ice, and admixed with a 10% hydrochloric acid to effect a decomposition reaction. The reaction mixture was thereafter concentrated under reduced pressure, neutralized with an aqueous sodium hydroxide solution, and extracted with chloroform to give crude crystalline (S)-(−)-N-p-hydroxybenzyl-α-phenyl-β-p-tolylethylamine, which was then recrystallized from ethyl alcohol, so that 2.37 g of the aimed product were obtained. Yield: 74.7%. m.p. 129.0°–130° C.; $[\alpha]_D^{25}$+19.6° (C 1.0, CHCl$_3$)

EXAMPLE 26

8.0 g (0.0476 mole) of (±)-cis/trans-mixed chrysanthemic acid (cis/trans=4.5/95.5) were dissolved in 8.0 g of toluene, and the resulting solution was added dropwise to a solution of 6.88 g (0.0285 mole) of (R)-(+)-N-(p-hydroxybenzyl)-1-(p-tolyl)ethylamine in 72 g of toluene under stirring at 70° C. The reaction mixture was cooled to 20° C. over 4 hours, and kept at this temperature for 30 minutes to precipitate a crystalline material, which was then separated by filtration, washed twice with 15 ml of toluene, and again separated by filtration to give 8.46 g of a crystalline product. Yield: 43.4%.

The crystalline product was decomposed with a 2% aqueous sodium hydroxide solution, and adjusted to a pH of from 8 to 9. Then an extraction operation was carried out twice with 50 ml of toluene, and the organic layer was concentrated under reduced pressure to recover 4.93 g of the (R)-(+)-N-(p-hydroxybenzyl)-1-(p-tolyl)ethylamine.

The aqueous layer was acidified with a 10% hydrochloric acid, extracted twice with 50 ml of toluene, and concentrated under reduced pressure to give 3.46 g of (+)-trans-chrysanthemic acid. Yield: 43.3%.

The (+)-trans-chrysanthemic acid thus obtained was converted into an ester of (S)-(+)-2-octanol, which was analysed by a gas chromatography. It was found that there were the following optical isomers in this ester product: 0.3% of (+)-cis-isomer, 0.2% of (−)-cis-isomer, 95.4% of (+)-trans-isomer, and 9.2% of (−)-trans-isomer. Yield (D/D): 82.8%.

EXAMPLES 27–32

The procedures shown in Example 26 were repeated, except that the cis/trans ratio of (±)-cis/trans-chrysanthemic acid was varied, that use was made of various optically active amine compounds and various solutions, and that the molar ratio of the amine compounds to the chrysanthemic acid was varied.

EXAMPLE 27

Materials used in reaction:

5.7 g (0.0339 mole) of (±)-cis/trans-mixed chrysanthemic acid (cis/trans=19.7/80.3); 4.87 g (0.0202 mole) of (R)-(+)-N-(p-hydroxybenzyl)-1-(p-tolyl)ethylamine; and 28.5 g of toluene.

Product:

The amount of (+)-trans-chrysanthemic acid obtained was 2.11 g. Yield (D/D): 70.1%.

The ratio of optical isomers: 1.7% of (+)-cis-isomer, 1.1% of (−)-cis-isomer, 93.0% of (+)-trans-isomer, and 4.2% of (−)-trans-isomer.

EXAMPLE 28

Materials used in reaction:

8.0 g (0.0476 mole) of (±)-cis/trans-mixed chrysanthemic acid (cis/trans=0.1/99.9); 6.88 g (0.0285 mole) of (R)-(+)-N-(p-hydroxybenzyl)-1-(p-tolyl)ethylamine; and 80 g of toluene.

Product:

The amount of (+)-trans-chrysanthemic acid obtained was 3.49 g. Yield (D/D): 86.3%.

The ratio of optical isomers: 0% of (+)-cis-isomer, 0% of (−)-cis-isomer, 98.9% of (+)-trans-isomer, and 1.1% of (−)-trans-isomer.

EXAMPLE 29

Materials used in reaction:

8.0 g (0.0476 mole) of (±)-cis/trans-mixed chrysanthemic acid (cis/trans=4.5/95.5); 8.59 g (0.0356 mole) of (R)-(+)-N-(p-hydroxybenzyl)-1-(p-tolyl)ethylamine; and 80 g of toluene.

Product:

The amount of (+)-trans-chrysanthemic acid obtained was 3.71 g. Yield (D/D): 87.7%.

The ratio of optical isomers: 0.4% of (+)-cis-isomer, 0.2% of (−)-cis-isomer, 94.1% of (+)-trans-isomer, and 5.3% of (−)-trans-isomer.

EXAMPLE 30

Materials used in reaction:

8.0 g (0.0476 mole) of (±)-cis/trans-mixed chrysanthemic acid (cis/trans=4.5/95.5); 6.88 g (0.0285 mole) of (R)-(+)-N-(p-hydroxybenzyl)-1-(p-tolyl)ethylamine; and 80 g of monochlorobenzene.

Product:

The amount of (+)-trans-chrysanthemic acid obtained was 3.55 g. Yield (D/D): 82.9%.

The ratio of optical isomers: 0.4% of (+)-cis-isomer, 0.2% of (−)-cis-isomer, 93.1% of (+)-trans-isomer, and 6.3% of (−)-trans-isomer.

EXAMPLE 31

Materials used in reaction:

8.0 g (0.0476 mole) of (±)-cis/trans-mixed chrysanthemic acid (cis/trans=4.5/95.5); 6.88 g (0.0285 mole) of (R)-(+)-N-(p-hydroxybenzyl)-1-(p-tolyl)ethylamine; and 80 g of methyl isobutyl ketone.

Product:

The amount of (+)-trans-chrysanthemic acid obtained was 3.40 g. Yield (D/D): 82.3%.

The ratio of optical isomers: 0.3% of (+)-cis-isomer, 0% of (−)-cis-isomer, 96.5% of (+)-trans-isomer, and 3.2% of (−)-trans-isomer.

EXAMPLE 32

Materials used in reaction:

8.0 g (0.0476 mole) of (±)-cis/trans-mixed chrysanthemic acid (cis/trans=4.5/95.5); 8.17 g (0.0359 mole) of (R)-(+)-N-(p-hydroxybenzyl)-1-phenylethylamine; and 64 g of isopropanol.

Product:

The amount of (+)-trans-chrysanthemic acid obtained was 2.52 g. Yield (D/D): 60.0%.

The ratio of optical isomers: 0.4% of (+)-cis-isomer, 0.3% of (−)-cis-isomer, 94.9% of (+)-trans-isomer, and 4.3% of (−)-trans-isomer.

EXAMPLE 33

1.68 g (0.01 mole) of (±)-cis/trans-mixed chrysanthemic acid and 2.77 g (0.01 mole) of (R)-(−)-N-(p-hydroxybenzyl)-1-(1-naphthyl)ethylamine were added to 8.4 g of isopropanol, and heated to 70° C. so as to dissolve these reactants in the isopropanol. The reaction solution was admixed with 1 mg of an (R)-(−)-N-(p-hydroxybenzyl)-1-(1-naphthyl)ethylamine salt of (+)-trans-chrysanthemic acid, and cooled to 20° C. over 4 hours. Then the reaction mixture was kept standing over night.

1.62 g of the crystalline material thus formed (yield: 36.4%) were separated by filtration, and decomposed with a 2% aqueous sodium hydroxide solution. The reaction mixture was adjusted to a pH of from 8 to 9, and extracted twice with 25 ml of chloroform. The organic layer was concentrated under reduced pressure to recover 0.99 g of (R)-(−)-N-(p-hydroxybenzyl)-1-(1-naphthyl)ethylamine.

The aqueous layer was acidified with a 10% sulfuric acid, extracted twice with 25 ml of toluene, and concentrated under reduced pressure to give 0.60 g of (+)-trans-chrysanthemic acid. Yield: 35.7%.

The (+)-trans-chrysanthemic acid thus obtained was converted into an ester of (S)-(+)-2-octanol, which was then analysed by a gas chromatography.

The ratio of the optical isomers: 0.6% of (+)-cis-isomer, 0.3% of (−)-cis-isomer, 96.4% of (+)-trans-isomer, and 2.7% of (−)-trans-isomer.

EXAMPLE 34–37

The procedures shown in Example 33 were repeated, except that use was made of various optically active amine compounds and also various solvents.

EXAMPLE 34

Materials used in reaction:

1.68 g (0.01 mole) of (±)-cis/trans-mixed chrysanthemic acid (cis/trans=4.5/95.5); 3.06 g (0.01 mole) of (R)-(+)-N-(p-hydroxybenzyl)-1-(p-bromophenyl)ethylamine; and 33.6 g of isopropanol.

Product:

The amount of (+)-trans-chrysanthemic acid obtained was 0.52 g. Yield (D/D): 60.0%. The ratio of optical isomers: 0.4% of (+)-cis-isomer, 0.4% of (−)-cis-isomer, 96.6% of (+)-trans-isomer, and 2.6% of (−)-trans-isomer.

EXAMPLE 35

Materials used in reaction:

1.68 g (0.01 mole) of (±)-cis/trans-mixed chrysanthemic acid (cis/trans=4.5/95.5); 2.17 g (0.01 mole) of (S)-(+)-N-(p-hydroxybenzyl)-1-cyclohexylethylamine; and 5.0 g of toluene.

Product:

The amount of (+)-trans-chrysanthemic acid obtained was 0.62 g. Yield (D/D): 65.2%. The ratio of optical isomers: 0.5% of (+)-cis-isomer, 0.3% of (−)-cis-isomer, 87.9% of (+)-trans-isomer, and 11.3% of (−)-trans-isomer.

EXAMPLE 36

Materials used in reaction:

1.68 g (0.01 mole) of (±)-cis/trans-mixed chrysanthemic acid (cis/trans=4.5/95.5); 3.06 g (0.01 mole) of (R)-(+)-N-(p-hydroxybenzyl)-1-(p-bromophenyl)ethylamine; and 13.9 g of methyl alcohol.

Product:

The amount of (+)-trans-chrysanthemic acid obtained was 0.53 g. Yield (D/D): 60.6%. The ratio of optical isomers: 0.2% of (+)-cis-isomer, 0.2% of (−)-cis-isomer, 95.9% of (+)-trans-isomer, and 3.7% of (−)-trans-isomer.

EXAMPLE 37

1.68 g (0 01 mole) of (±)-cis/trans-mixed chrysanthemic acid (cis/trans=4.5/95.5); 2.25 g (0.01 mole) of (R)-(+)-N-(p-hydroxybenzyl)-1-(p-tolyl)ethylamine; and 126 g of toluene.

Product:

The amount of (+)-trans-chrysanthemic acid obtained was 0.69 g. Yield (D/D): 80.7%. The ratio of optical isomers: 0.4% of (+)-cis-isomer, 0.3% of (−)-cis-isomer, 97.8% of (+)-trans-isomer, and 1.5% of (−)-trans-isomer.

EXAMPLE 38

1.68 g (0.01 mole) of (±)-cis/trans-mixed chrysanthemic acid (cis/trans=4.5/95.5) and 3.02 g (0.01 mole) of (R)-(+)-N-(2-hydroxy-3-methoxy-benzyl)- 1-(p-nitrophenyl)ethylamine were added to 17.0 g of toluene, and heated to 70° C. so as to dissolve these reactants in the toluene. The reaction mixture thus formed was admixed with I mg of an (R)-(+)-N-(2-hydroxy- 3-methoxybenzyl)-1-(p-nitrophenyl)ethylamine salt of (+)-trans-chrysanthemic acid, and cooled to 20° C. over 4 hours. Then the reaction mixture was kept standing over night.

The crystalline material thus formed was separated off by filtration. The amount of the crystalline material obtained was 1.98 g (yield: 42.1%). The crystalline material was decomposed with 1% hydrochloric acid, and then an extraction operation was effected twice with 20 ml of toluene. The organic layer was concentrated under reduced pressure to give 0.69 g of (+)-trans-chrysanthemic acid (yield: 41.1%).

The aqueous layer was decomposed with a 2% aqueous sodium hydroxide solution, adjusted to a pH of from 8 to 9, and extracted twice with 20 ml of toluene. The organic layer thus obtained was concentrated under reduced pressure to recover 1.22 g of (R)-(+)-N-( 2-hydroxy-3-methoxybenzyl)-1-(p-nitrophenyl)ethylamine.

The (+)-trans-chrysanthemic acid thus obtained was converted into an ester of (S)-(+)-2-octanol, which was then analysed by a gas chromatography. The analytical results concerning the optical isomers were as follows: 1.7% of (+)-cis-isomer, 0% of (−)-cis-isomer, 96.8% of (+)-trans-isomer, and 1.5% of (−)-trans-isomer. Yield (D/D): 80.9%.

EXAMPLES 39–43

The procedures shown in Example 38 were repeated, except that use was made of various optically active amine compounds and also various solvents.

EXAMPLE 39

1.68 g (0.01 mole) of (±)-cis/trans-mixed chrysanthemic acid (cis/trans=4.5/95.5); 2.71 g (0.01 mole) of (R)-(+)-N-(2-hydroxy-3-methoxybenzyl)-1-phenylethylamine; and 9.7 g of toluene.

Product:

The amount of (+)-trans-chrysanthemic acid obtained was 0.57 g. Yield (D/D): 65.9%. The ratio of optical isomers: 0.5% of (+)-cis-isomer, 0.2% of (−)-cis-isomer, 96.6% of (+)-trans-isomer, and 2.8% of (−)-trans-isomer.

EXAMPLE 40

Materials used in reaction: 1.68 g (0.01 mole) of (±)-cis/trans-mixed chrysanthemic acid (cis/trans=4.5/95.5); 2.72 g (0.01 mole) of (R)-(+)-N-(p-hydroxybenzyl)ethylamine; and 60 g of toluene.

Product:

The amount of (+)-trans-chrysanthemic acid obtained was 0.69 g. Yield (D/D): 80.6%. The ratio of optical isomers: 1.0% of (+)-cis-isomer, 0.3% of (−)-cis-isomer, 97.1% of (+)-trans-isomer, and 1.6% of (−)-trans-isomer.

EXAMPLE 41

Materials used in reaction:

1.68 g (0.01 mole) of (±)-cis/trans-mixed chrysanthemic acid (cis/trans=4.5/95.5); 2.72 g (0.01 mole) of (R)-(+)-N-(p-hydroxybenzyl)-1-(p-nitrophenyl)ethylamine; and 12.1 g of isopropanol.

Product:

The amount of (+)-trans-chrysanthemic acid obtained was 0.63 g. Yield (D/D): 71.9%. The ratio of optical isomers: 0.7% of (+)-cis-isomer, 0.5% of (−)-cis-isomer, 95.1% of (+)-trans-isomer, and 3.8% of (−)-trans-isomer.

EXAMPLE 42

Materials used in reaction:

1.68 g (0.01 mole) of (±)-cis/trans-mixed chrysanthemic acid (cis/trans=4.5/95.5); 3.02 g (0.01 mole) of (R)-(+)-N-(2-hydroxy-3-methoxybenzyl)-1 -(p-tolyl)ethylamine; and 6.4 g of toluene.

Product:

The amount of (+)-trans-chrysanthemic acid obtained was 0.52 g. Yield (D/D): 59.8%. The ratio of optical isomers: 0.7% of (+)-cis-isomer, 0.2% of (−)-cis-isomer, 95.9% of (+)-trans-isomer, and 3.2% of (−)-trans-isomer.

EXAMPLE 43

Materials used in reaction:

1.68 g (0.01 mole) of (±)-cis/trans-mixed chrysanthemic acid (cis/trans=4.5/95.5); 3.02 g (0.01 mole) of (R)-(+)-N-(2-hydroxy-3-methoxybenzyl)-1 -(p-tolyl)ethylamine; and 8.6 g of isopropanol.

Product:

The amount of (+)-trans-chrysanthemic acid obtained was 0.52 g. Yield (D/D): 60.7%. The ratio of optical isomers: 0.8% of (+)-cis-isomer, 0% of (−)-cis-isomer, 97.3% of (+)-trans-isomer, and 1.9% of (−)-trans-isomer.

EXAMPLE 44

1.68 g (10 millimoles) of (±)-cis-trans-mixed chrysanthemic acid (cis/trans=4.5/95.5) and 3.17 g (10 millimoles) of (R)-(+)-N-p-hydroxybenzyl-α-phenyl-β -p-tolylethylamine were added to 43.92 g of toluene, and heated to 70°

C. so as to dissolve these reactants in the toluene. Thereafter, a cooling operation was started for the reaction mixture. At 50° C., about 1 mg of an (R)-(+)-N-p-hydroxybenzyl-α-phenyl-β-p-tolylethylamine salt of (+)-trans-chrysanthemic acid was added to the reaction mixture, which was then cooled to 20° C. over 2 hours, and thereafter kept standing over night.

2.30 g of the crystalline material thus formed were separated by filtration (yield: 47.4%), and decomposed with a 2% aqueous sodium hydroxide solution. Then an extraction operation was effected three times with 40 ml of toluene. The organic layer was concentrated under reduced pressure to recover 1.50 g of (R)-(+)-N-p-hydroxybenzyl-α-phenyl-β-p-tolylethylamine. The aqueous layer was acidified with 7 ml of a 10% hydrochloric acid, extracted with 20 ml of toluene, and concentrated under reduced pressure to give 0.79 g of (+)-trans-chrysanthemic acid. Yield 47.0%. Yield (d/d): 91.3%.

The (+)-trans-chrysanthemic acid thus obtained was converted into an ester of (S)-(+)-2-octanol, which was analysed by a gas chromatography. The analytical results concerning the optical isomers were as follows: 1.3% of (+)-cis-isomer, 0.6% of (−)-cis-isomer, 95.8% of (+)-trans-isomer, and 2.3% of (−)-trans-isomer.

EXAMPLES 45–47

The procedures shown in Example 44 were repeated, except that the cis/trans ratio of (+)-cis/trans-chrysanthemic acid was varied, and that the molar ratio of (±)-cis/trans-chrysanthemic acid to (R)-(+)-N-p-hydroxybenzyl-α-phenyl-β-p-tolylethylamine was also varied. The results of these experiments are shown in Table 1.

The material, which had crystalline out, was separated by filtration. The amount of the crystalline material thus obtained was 1.47 g (yield: 31.3%). The crystalline material was decomposed with a 1% hydrochloric acid, and then an extraction operation was carried out twice with 20 ml of toluene. The organic layer was concentrated under reduced pressure to give 0.66 g of (S)-(+)-2-(4-chlorophenyl)isovaleric acid. Yield: 31%.

The ratio of the optical isomers: 95.3% of (S)-(+)-isomer, and 4.7% of (R)-(−)-isomer.

EXAMPLE 49

2.09 g (0.01 mole) of (±)-cis-permethric acid and 2.27 g (0.01 mole) of (R)-(+)-N-(p-hydroxybenzyl)-1-phenylethylamine were added to 1.5 g of isopropanol, and heated to 70° C. so as to dissolve these reactants in the isopropanol. The reaction mixture was cooled to 20° C. over 4 hours, and then kept standing at this temperature over night.

The material, which has crystallized out, was separated by filtration. The amount of the crystalline material thus obtained was 1.76 g (yield: 40.3%). The crystalline material was decomposed with a 1% hydrochloric acid, and then an extraction operation was carried out twice with 20 ml of toluene. The organic layer was concentrated under reduced pressure to give 0.84 g of (+)-cis-permethric acid. Yield: 40.2%.

The ratio of the optical isomers: 98.8% of (+)-cis-isomer, and 1.2% of (−)-cis-isomer.

EXAMPLE 50

2.53 g (0.01 mole) of (±)-ketoprofen and 2.27 g (0.01 mole) of (S)-(−)-N-(p-hydroxybenzyl)-1-phenylethylamine

TABLE 1

| | Amount used (g) | | | (+)-chrysanthemic acid | | | | |
|---|---|---|---|---|---|---|---|---|
| | | Optically | | Amount | Ratio of optical isomers | | | |
| Ex. No. | (±)-chrysan-themic acid | active amine | Solvent | obtained (g) | (+)-cis | (−)-cis | (+)-trans | (−)-trans |
| 44 | 1.68 (10 mmol) (cis/trans = 4.5/95.5) | 3.17 (10 mmol) | Toluene 43.92 | 0.79 (Y(d/d) = * 91.3%) | 1.3 | 0.6 | 95.6 | 2.3 |
| 45 | 0.84 (5 mmol) (cis/trans = 4.5/95.5) | 0.79 (2.5 mmol) | Toluene 12.60 | 0.36 (Y(d/d) = 84.3%) | 0.7 | 0.4 | 97.6 | 1.3 |
| 46 | 0.84 (5 mmol) (cis/trans = 20.3/79.7) | 1.58 (5 mmol) | Toluene 12.60 | 0.30 (Y(d/d) = 68.8%) | 5.5 | 2.7 | 90.8 | 1.0 |
| 47 | 1.68 (10 mmol) (cis/trans = 0/100) | 3.17 (10 mmol) | Toluene 44.0 | 0.81 (Y(d/d) = 93.9%) | — | — | 97.4 | 2.6 |

*Y(d/d) ... Yield (d/d)

EXAMPLE 48

2.13 g (0.01 mole) of (±)-2-(4-chlorophenyl)isovaleric acid and 2.57 g (0.01 mole) of (R)-(+)-N-(2-hydroxy-3-methoxybenzyl)-1-phenylethylamine were added to 8.5 g of toluene, and heated to 70° C. so as to dissolve these reactants in the toluene. The reaction mixture was cooled to 20° C. over 4 hours, and then kept standing at this temperature over night.

were added to 9.1 g of methanol, and heated to 60° C. so as to dissolve these reactants in the methanol. The reaction mixture was cooled to 20° C. over 4 hours, and then kept standing at this temperature over night.

The material, which had crystallized out, was separated by filtration. The amount of the crystalline material thus obtained was 2.09 g (yield: 43.5%). The crystalline material was decomposed with a 1% hydrochloric acid, and then an extraction operation was carried out twice with 20 ml of toluene. The organic layer was concentrated under reduced pressure to give 1.09 g of (+)-ketoprofen. Yield: 43.1%.

The specific rotation of this substance $[\alpha]_D^{21}$: +31.7° (C 1.0, chloroform). The ratio of optical isomers: 79.1% of (S)-(+)-isomer, and 20.9% of (R)-(−)-isomer.

EXAMPLE 51

In this experiment, use was made of the chrysanthemic acid shown in Example 33. A solution of 16 g (0.0952 mole) of the chrysanthemic acid in 15.5 g of toluene was added at 65° C. under stirring to a solution of 24.47 g (0.0951 mole) of (R)-(+)-N-(2-hydroxy-3-methoxybenzyl)-1-phenylethylamine in 24.5 g of toluene. Thereafter, a cooling operation was started for the reaction mixture. 5 mg of an (R)-(+)-N-(2-hydroxy-3-methoxybenzyl)-1-phenylethylamine salt of (+)-trans-chrysanthemic acid were added to the reaction mixture under cooling.

After a material had crystallized out, the reaction mixture was kept at 58° C. for 1 hour, cooled to 20° C. over 4 hours, and stirred at the latter temperature for 30 minutes.

The crystalline material was separated out by filtration, washed twice with 7 g of toluene, and decomposed with a 1% hydrochloric acid. Then, an extraction operation was carried out twice with 50 g of toluene. The organic layer was concentrated under reduced pressure to give 6.34 g of (+)-trans-chrysanthemic acid. Yield: 39.6%. Yield (D/D): 76.2%. The ratio of optical isomers: 0.5% of (+)-cis-isomer, 0.2% of (−)-cis-isomer, 95.7% of (+)-trans-isomer, and 3.7% of (−)-trans-isomer.

EXAMPLE 52

The procedures shown in Example 33 were repeated, except that 2.27 g (0.01 mole) of (R)-(+)-N-(p-hydroxybenzyl)-1-phenylethylamine were used instead of (R)-(−)-N-(p-hydroxybenzyl)-1-(1-naphthyl)ethylamine, and that 33.6 g of toluene were employed instead of isopropanol.

0.55 g of (+)-trans-chrysanthemic acid was obtained. Yield: 32.7%. Yield (D/D): 64.8%. The ratio of optical isomers: 0.6% of (+)-cis-isomer, 0% of (−)-cis-isomer, 98.3% of (+)-trans-isomer, and 1.1% of (−)-trans-isomer.

Comparative Example 1

The procedures shown in Example 52 were repeated, except that 1.21 g (0.01 mole) of (R)-(+)-α-phenylethylamine were used instead of (R)-(+)-N-(p-hydroxybenzyl)-1-phenylethylamine, and that 16 g of toluene were employed.

1.23 g of chrysanthemic acid were obtained. Yield: 73.2%. Yield (D/D): 59.9%. The ratio of the optical isomers: 0.3% of (+)-cis-isomer, 0.4% of (−)-cis-isomer, 40.6% of (+)-trans-isomer, and 53.3% of (−)-trans-isomer.

Comparative Example 2

The procedures shown in Example 52 were repeated, except that 2.27 g (0.01 mole) of (R)-(+)-N-(o-hydroxybenzyl)-1-phenylethylamine were used instead of (R)-(+)-N-(p-hydroxybenzyl)-1-phenylethylamine, and that 5 g of toluene were employed.

There were no materials crystallized out.

Comparative Example 3

The procedures shown in Example 52 were repeated, except that 2.77 g (0.01 mole) of (R)-(+)-N-(o-hydroxybenzyl)-1-naphthylethylamine were used instead of (R)-(+)-N-(p-hydroxybenzyl)-1-phenylethylamine, and that 5 g of toluene was employed.

There were no materials crystallized out.

Comparative Example 4

The procedures shown in Example 44 were repeated, except that 2.11 g (0.01 mole) of (S)-(+)-α-phenyl-β-p-tolylethylamine were used instead of (R)-(+)-N-(p-hydroxybenzyl)-α-phenyl-β-p-tolylethylamine, and that 21.8 g of toluene were employed.

1.18 g of (+)-trans-chrysanthemic acid were obtained. Yield: 70.2%. Yield (D/D): 74.4%. The ratio of optical isomers: 1.7% of (+)-cis-isomer, 1.5% of (−)-cis-isomer, 52.0% of (+)-trans-isomer, and 44.8% of (−)-trans-isomer.

Comparative Example 5

The procedures shown in Example 44 were repeated, except that 0.95 g (0.045 mole) of (S)-(+)-α-phenyl-β-p-tolylethylamine was used instead of (R)-(+)-N-p-hydroxybenzyl-α-phenyl-β-p-tolylethylamine, and that 5.9 g of toluene were employed.

0.42 g of (+)-trans-chrysanthemic acid was obtained. Yield: 25%. Yield (D/D): 47.4%. The ratio of optical isomers: 2.3% of (+)-cis-isomer, 0% of (−)-cis-isomer, 92.5% of (+)-trans-isomer, and 5.2% of (−)-trans-isomer.

EXAMPLE 53

1.52 g (0.01 mole) of (±)-mandelic acid and 2.57 g (0.01 mole) of (S)-(−)-N-(2-hydroxy-3-methoxybenzyl)-1-phenylethylamine were added to 6.84 g of toluene, and heated to 70° C. so as to dissolve these reactants in the toluene. The reaction mixture was cooled to 20° C. over 4 hours, and kept standing at this temperature over night.

The material, which had crystallized out, was separated off by filtration. The amount of the crystalline material thus obtained was 1.64 g (yield: 40.1%).

The crystalline material was decomposed with a 1% hydrochloric acid, and an extraction operation was carried out twice with 20 ml of diethyl ether. The organic layer was concentrated under reduced pressure to give 0.59 g of (−)-mandelic acid. Yield: 38.8%, $[\alpha]_D^{20}$: 152.8° (C 2.8, H₂O) The ratio of optical isomers: 1,4% of (+)-isomers, and 98,6% of (−)-isomer.

We claim:

1. A process of using an optically active secondary amine compound for the preparation of an optically active carboxylic acid, wherein an optically active secondary amine compound of the general formula (I):

wherein $R_1$ represents a naphthyl or cyclohexyl group, or a phenyl group optionally substituted by halogen, nitro, lower alkyl or lower alkoxy, $R_2$ represents a lower alkyl group or a benzyl group optionally substituted by lower alkyl, $R_3$ represents a p-hydroxyphenyl or 2-hydroxy-3-lower alkoxyphenyl group when $R_2$ is lower alkyl, or $R_3$ represents a p-hydroxyphenyl group when $R_2$ is benzyl optionally substituted by lower alkyl, and C* represents an asymmetric carbon atom, is reacted with a racemic carboxylic acid selected from the group consisting of (±)-chrysanthemic acid, (±)-ibuprofen, (±)-naproxen, (±)-flurbiprofen, (±)-ketoprofen, (±)-2-(4-chlorophenyl)isovaleric acid, (±)-mandelic acid, (±)-2-hydroxy-4-phenylbutanoic acid and (±)-permethric acid, and the resultant amine salt is then subjected to an optical resolution operation.

2. A process according to claim 1, wherein the racemic carboxylic acid is (±)-chrysanthemic acid.

3. A process according to claim 2, wherein the (±)-chrysanthemic acid is (±)-trans-chrysanthemic acid or (±)-cis/trans-mixed chrysanthemic acid.

4. A process according to claim 1, wherein the racemic carboxylic acid is (±)-permethric acid.

5. A process according to claim 4, wherein the (±)-permethric acid is (±)-trans-permethric acid or (±)-cis-permethric acid.

6. A process according to claim 1, wherein the racemic carboxylic acid is (±)-ketoprofen.

7. A process according to claim 1, wherein the racemic carboxylic acid is (±)-mandelic acid.

8. A process according to claim 1, wherein the racemic carboxylic acid is (±)-2-(4-chlorophenyl)isovaleric acid.

9. A process according to claim 1, wherein $R_1$ represents naphthyl, cyclohexyl, phenyl, o-, m- or p-chlorophenyl, o-, m- or p-bromophenyl, o-, m- or p-nitrophenyl, o-, m- or p-tolyl, o-, m- or p-ethylphenyl, o-, m- or p-propylphenyl, o-, m- or p-methoxyphenyl, o-, m- or p-ethoxyphenyl, or o-, m- or p-propoxyphenyl.

10. A process according to claim 1, wherein $R_2$ represents methyl, ethyl, propyl, butyl, pentyl, benzyl, o-, m- or p-tolylmethyl, o-, m- or p-ethylphenylmethyl, o-, m- or p-propylphenylmethyl, o-, m- or p-butylphenylmethyl, or o-, m- or p-pentylphenylmethyl.

11. A process according to claim 1, wherein $R_3$ represents p-hydroxyphenyl, 2-hydroxy-3-methoxyphenyl, 2-hydroxy-3-ethoxyphenyl, 2-hydroxyl-3-propoxyphenyl, 2-hydroxy-3-butoxyphenyl or 2-hydroxy-3-pentoxyphenyl.

12. A process according to claim 1, wherein the optically active secondary amine compound (I) is N-(p-hydroxybenzyl)-1-phenylethylamine, N-(p-hydroxybenzyl)-1-(p-tolyl)ethylamine, N-(p-hydroxybenzyl)-1-(p-isopropylphenyl)ethylamine, N-(p-hydroxybenzyl)-1-(p-nitrophenyl)ethylamine, N-(p-hydroxybenzyl)-1-(p-bromophenyl)ethylamine, N-(p-hydroxybenzyl)-1-(1-naphthyl)ethylamine, N-(p-hydroxybenzyl)-1-cyclohexylethylamine, N-(p-hydroxybenzyl)-1-(p-methoxyphenyl)ethylamine, N-(2-hydroxy-3-methoxybenzyl)-1-phenylethylamine, N-(2-hydroxy-3-methoxybenzyl)-1-(p-tolyl)ethylamine, N-(2-hydroxy-3-methoxybenzyl)-1-(p-isopropylphenyl)ethylamine, N-(2-hydroxy-3-methoxybenzyl)-1-(p-nitrophenylethylamine, N-(2-hydroxy-3-methoxybenzyl)-1-(p-bromophenyl)ethylamine, N-(2-hydroxy-3-methoxybenzyl)-1-(1-naphthyl)ethylamine, N-(2-hydroxy-3-methoxybenzyl)- 1-cyclohexylethylamine, N-(2-hydroxy-3-methoxybenzyl)- 1-(p-methoxyphenyl)ethylamine or N-(p-hydroxybenzyl)-α-phenyl-β-p-tolylethylamine.

* * * * *